United States Patent [19]
Zukowski et al.

[11] Patent Number: 4,914,031
[45] Date of Patent: Apr. 3, 1990

[54] SUBTILISIN ANALOGS

[75] Inventors: Mark M. Zukowski, Thousand Oaks, Calif.; Yitzhak Stabinsky, Boulder, Colo.; Michael Levitt, London, England

[73] Assignee: Amgen, Inc., Thousand Oaks, Calif.

[21] Appl. No.: 36,872

[22] Filed: Apr. 10, 1987

[51] Int. Cl.[4] .................. C12N 9/56; C12N 9/54; C12N 15/00
[52] U.S. Cl. ......................... 435/222; 435/172.1; 435/172.3; 435/220; 435/221; 935/14; 935/74; 935/82
[58] Field of Search ............ 435/172.1, 172.3, 221, 435/222, 320; 935/14

[56] References Cited
U.S. PATENT DOCUMENTS
4,760,025 7/1988 Estell et al. .................. 435/222

OTHER PUBLICATIONS
Thomas et al., Nature, 318: 375, 1985.

Primary Examiner—Thomas D. Mays
Attorney, Agent, or Firm—Thomas E. Byrne; Steven M. Odre

[57] ABSTRACT

A class of subtilisin analogs suitable for admixture to cleaning compositions and having improved stability over naturally occurring Bacillus subtilisins are prepared by expressing a modified gene encoding the subtilisin analog in *Bacillus subtilis*. The subtilisin analogs are characterized as having a modified calcium binding site to improve calcium binding and either an Asn or a Gly replaced in any Asn-Gly sequences present in the subtilisin.

22 Claims, 5 Drawing Sheets

SUBTILISIN ANALOGS

BACKGROUND OF THE INVENTION

The present invention provides a novel class of thermally stable and pH stable subtilisin analogs and to a method for preparing such analogs. In particular, the present invention relates to a class of subtilisin analogs having a modified calcium binding site providing improved calcium binding capacity and optionally a deletion and/or replacement of either residue of Asn-Gly sequences present in the subtilisin. The present invention further relates to detergent compositions containing such subtilisins and to the use of such subtilisins and compositions in cleaning applications.

The term subtilisin designates a group of extracellular alkaline serine proteases produced by various species of Bacilli. These enzymes are also referred to as Bacillus serine proteases, Bacillus subtilisins or bacterial alkaline proteases.

Bacillus subtilisin molecules are composed of a single polypeptide chain of either 274 residues (for subtilisin type Carlsberg produced by *Bacillus licheniformis* and for the subtilisin produced by *Bacillus subtilis* strain DY) or 275 residues (for subtilisin type BPN' produced by *Bacillus amyloliquefaciens*, the aprA gene product of *Bacillus subtilis*, and the subtilisin of *Bacillus mesentericus*). When comparing amino acid sequences of subtilisin from different strains of Bacillus herein, the sequence of subtilisin BPN' is used as a standard. For example, based on an alignment of sequences that gives the highest degree of homology between subtilisin Carlsberg and subtilisin BPN', the serine at the active site of the former is referred to a serine 221, even though it is located at position 220 of the amino acid sequence. On the same basis, position 220 of the amino acid sequence of subtilisin Carlsberg may be said to "correspond" to position 221 of subtilisin BPN'. See e.g., Nedkov et al., *Hoppe-Seyler's Z. Physiol. Chem.*, 364, 1537–1540 (1983).

The X-ray structure of subtilisin BPN' [Wright, et al., *Nature*, 221, 235 (1969)] revealed that the geometry of the catalytic site of subtilisin, involving $Asp^{32}$, $His^{64}$ and $Ser^{221}$, is almost identical to that of the active site of mammalian serine proteases (e.g., chymotrypsin) involving the residues $Asp^{102}$, $His^{57}$, and $Ser^{195}$. However, the overall dissimilarities between Bacillus serine proteases and mammalian serine proteases indicate that these are two unrelated families of proteolytic enzymes.

In the family of Bacillus subtilisins complete amino acid sequences are available for five subtilisins: Carlsberg, [Smith, et al., *J. Biol. Chem.*, 243, 2184–2191 (1968)]; BPN' [Markland, et al., *J. Biol. Chem.*, 242, 5198–5211 (1967)]; the aprA gene product [Stahl, et al., *J. Bacteriol.*, 158, 411–418 (1984)]; DY [Nedkov, et al., supra] and *Bacillus mesentericus*[Svendsen, et al., *FEBS Letters*, 196, 220–232 (1986)]. Subtilisin Carlsberg and subtilisin BPN' (sometimes referred to as subtilisin Novo) differ by 84 amino acids and one additional residue in BPN' (subtilisin Carlsberg lacks an amino acid residue corresponding to residue 56 of subtilisin BPN'). Subtilisin DY comprises 274 amino acids and differs from subtilisin Carlsberg in 32 amino acid positions and from subtilisin BPN' by 82 amino acid replacements and one deletion (subtilisin DY lacks an amino acid residue corresponding to residue 56 of subtilisin BPN'). The amino acid sequence of the aprA gene product is 85% homologous to the amino acid sequence of subtilisin BPN'. Thus, it appears that there is an extensive homology between amino acid sequences of subtilisins from different strains of Bacillus. This homology is complete in certain regions of the molecule and especially in those that play a role in the catalytic mechanism and in substrate binding. Examples of such sequence invariances are the primary and secondary substrate binding sites, $Ser^{125}$-$Leu^{126}$-$Gly^{127}$-$Gly^{128}$ and $Tyr^{104}$ respectively and the sequence around the reactive serine (221), $Asn^{218}$-$Gly^{219}$-$Thr^{220}$-$Ser^{221}$-$Met^{222}$-$Ala^{223}$.

Subtilisin molecules exhibit unique stability properties. Although they are not completely stable over a wide pH range, subtilisins are relatively resistant to denaturation by urea and guanidine solutions and their enzymatic activity is retained for some time in 8M urea. In solutions having a pH below 4, subtilisin rapidly and irreversibly loses its proteolytic activity. Gounaris, et al., *Compt. Rend. Trav. Lab. Carlsberg*, 35, 37 (1965) demonstrated that the acid deactivation of subtilisin is not due to a general charge effect and speculated that it is due to other changes in the molecule, such as protonation of histidine residues in the interior, hydrophobic parts of the molecule. Bacillus subtilisins undergo irreversible inactivation in aqueous solutions at a rate that is largely dependent upon temperature and pH. At pH values below 4 or above 11 the rate of inactivation is very rapid while at pH's of between 4.5 and 10.5 the rate, although much slower, increases as the solution becomes more alkaline. The mechanisms of this inactivation are not fully known but there is evidence indicating that autodigestion is responsible at least in part for enzyme instability at this pH range. In general, at any pH value, the higher the temperature the faster the rate of subtilisin deactivation.

The use of proteases in industrial processes which require hydrolysis of proteins has been limited due to enzyme instability under operational conditions. Thus, for example, the incorporation of trypsin into laundry detergents (e.g., Bio-38, Schnyder; Switzerland) to facilitate removal of proteinaceous stains had a very limited success which was undoubtedly a result of enzyme instability under the washing conditions. In addition, bacterial alkaline proteases compatible with detergents have been utilized in detergent formulations.

Because many industrial processes are conducted at temperatures that are above the stability range of most enzymes, highly thermostable proteases not only will be advantageous to certain industries such as detergent and hide dehairing, that already require stable proteases, but may be useful in industries that use chemical means to hydrolyze proteins e.g. hydrolysis of vegetable and animal proteins for the production of soup concentrates.

Although thermal inactivation may be the most important factor in restricting the industrial use of enzymes, other factors such as need for effectiveness over broad pH ranges and use of denaturing agents may also have a detrimental effect with respect to the use of proteases in industrial processes. It is therefore desirable to obtain a class of proteases characterized by improved stability with respect to temperature, pH, denaturing agents and other conditions required by various industries.

Over the past several years there have been major changes in detergent formulations, particularly in the replacement of phosphates with alternate builders and in the development of liquid laundry detergents to meet environmental and consumer demands. These changes create a need for changes in traditional detergent enzymes. More particularly, it has become desirable to employ proteolytic enzymes which possess greater storage stability in liquid laundry formulations as well as stability and activity at broader ranges of pH and temperature.

One approach to producing modified subtilisins useful in detergent formulations was disclosed in European patent application No. 130,756, wherein mutations in the subtilisin of *Bacillus amyloliquefaciens* (*B. amyloliquefacines*) at positions $Tyr^{-1}$, $Asp^{32}$, $Asn^{155}$, $Tyr^{104}$, $Met^{222}$, $Gly^{166}$, $His^{64}$, $Gly^{169}$, $Phe^{189}$, $Ser^{33}$, $Ser^{221}$, $Tyr^{217}$, $Glu^{156}$, and/or $Ala^{152}$ were identified as providing changed stability, altered conformation or as having changes in the "processing" of the enzyme. In particular, a mutation of $Met^{222}$ to Ala or Cys (which mutant also exhibits a sharper pH optimum than wild type) or Ser assertedly resulted in improved oxidation stability. It was suggested that substitution for $Gly^{166}$ with Ala, Asp, Glu, Phe, His, Lys, Asn, Arg or Val would alter the kinetic parameters of the enzyme. However, none of the mutations disclosed provide analogs having greater stability at high temperatures or stability over a broader pH range than the wild type enzyme.

In another approach, Thomas, et al, *Nature* 318, 375–376 (1985), disclosed that the pH dependence of subtilisin may be altered by changing an Asp to Ser in $Asp^{99}$-$Gly^{100}$ of subtilisin BPN'. This change represents an alteration of a surface charge 14–15 Angstroms from the active site. However, Thomas, et al. fails to provide any indication of improvement where no change in surface charge is made, as is the case where one uncharged residue is substituted for another.

A third approach, described in co-pending U.S. application Ser. No. 819,241 now abandoned, relates to a class of Bacillus serine protease analogs characterized by deletion and/or modifications of any Asn-Gly sequences present in the protease.

SUMMARY OF THE INVENTION

The present invention provides a class of subtilisin analogs characterized as having improved pH and thermal stability thereby rendering such analogs especially useful in detergent formulations as well as other processes requiring stable proteases. The subtilisin analogs according to the present invention are characterized as having an amino acid sequence of a naturally occurring Bacillus subtilisin that has been modified by having (1) one or more amino acid residues in a calcium binding site present in the amino acid sequence of the naturally occurring Bacillus subtilisin replaced with a negatively charged amino acid, and (2) either residue of any Asn-Gly sequence present in the amino acid sequence of the naturally occurring Bacillus subtilisin deleted or replaced. The present invention further provides detergent compositions comprising the subtilisin analogs of the present invention and to the use of such subtilisin analogs and compositions in cleansing applications.

The subtilisin analogs of the present invention exhibit improved thermal and pH stability, increased specific activity and broad substrate specificity thereby increasing the detergency of detergent formulations containing such analogs. In particular, the subtilisin analogs of the present invention provide improved thermostability, increased pH stability and higher specific activity than found in "wild type" subtilisins.

In addition, the present invention relates to DNA sequences having codons encoding a subtilisin analog as described above.

The present invention also provides a process for the production of subtilisin analogs comprising a host cell having nucleic acid encoding a subtilisin analog as described above. In such a cell, the nucleic acid encoding the subtilisin analog may be chromosomal or extrachromosomal. The host call is preferably selected from a strain deficient in secreted proteases, allowing for facile isolation of the analogs of the present invention.

In addition, the present invention provides a method for improving the thermal and pH stability of subtilisins by modifying the calcium binding site and/or substituting an amino acid other than asparagine for an asparagine in an Asn-Gly sequence and in particular for the asparagine residue at the position in the amino acid sequence of the subtilisin which corresponds to position 218 in the amino acid sequence as disclosed in Table 1.

DETAILED DESCRIPTION

Figure 1:
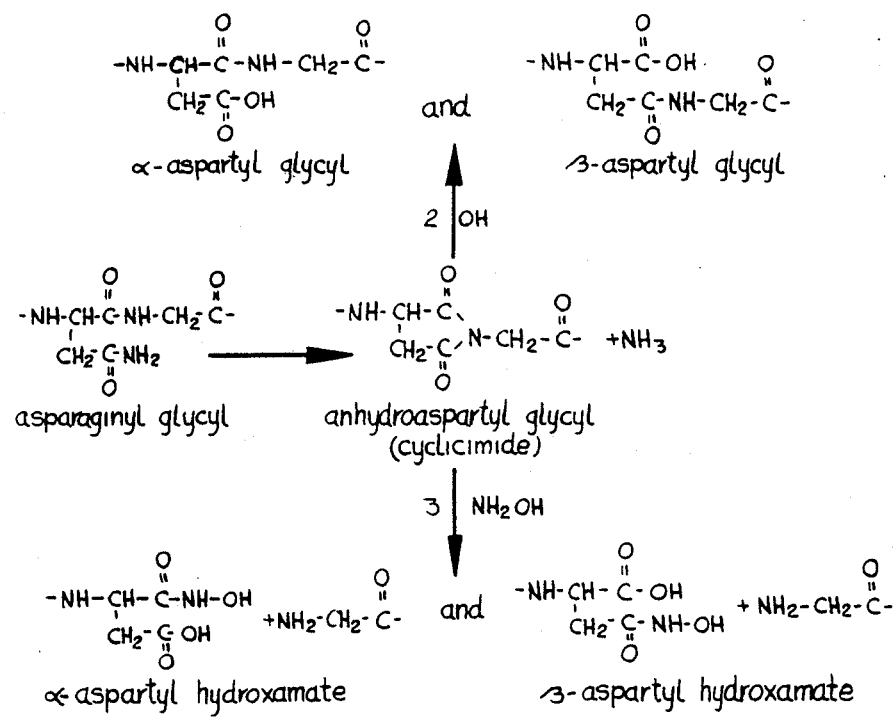
FIG. 1 schematically illustrates the cyclization of Asn-Gly residues, such as those found at positions 218 and 219 of subtilisin as set forth in Table 1, to form anhydroaspartylglycine and also depicts base-catalyzed hydrolysis thereof.

It should be noted that, as employed herein, the term "subtilisin" refers to a mature, secreted form of the enzyme which lacks leader sequences cleaved from the mature enzyme prior to or at secretion. Representative of subtilisins that may be modified in accordance with the present invention include but is not limited to naturally occurring subtilisins represented by the amino acid sequence of subtilisin Carlsberg, subtilisin BPN', the aprA gene product of *Bacillus subtilis*, subtilisin DY and the subtilisin of *Bacillus mesentericus*. The amino acid sequence for subtilisin Carlsberg is described by Smith, et al., *J. Biol. Chem.*, 243, 2184–2191 (1968). The amino acid sequence for subtilisin BPN' is described by Markland, et al., *J. Biol. Chem.*, 242, 5198–5211 (1967). The amino acid sequence for subtilisin DY is described by Nedlov, et al., *Hoppe-Seyler's Z. Physiol. Chem.*, 364, 1537–1540 (1983). The amino acid sequence for the subtilisin of *Bacillus mesentericus* is described by Svedsen, et al., *FEBS Letters*, 196, 220–232 (1986). The amino acid sequence of the aprA gene product of *Bacillus subtilis* is described by Stahl, et al., *J. Bacteriol.*, 158, 411–418 (1984). The amino acid sequence of such subtilisins are incorporated by reference herein. Such subtilisins are characterized as having calcium binding sites necessary to stabilize the molecule.

In accordance with the present invention, a class of subtilisin analogs are provided which possess improved capacity to bind to calcium. Calcium has been used to stabilize subtilisin in powders and liquid detergent, especially in applications requiring higher temperatures. The present invention relates to the modification of the calcium binding site of the subtilisin molecule to increase calcium binding. As used herein the term "modification of the calcium binding site" refers to replacement of one or more amino acids in the region of a calcium binding site present in the amino acid sequence of subtilisin with a negatively charged amino acid thereby enabling the resulting subtilisin analog to have an additional negative charge. It has been found that one calcium binding site is a subtilisin involves the following amino acids: $Asp^{41}$, $Leu^{75}$, $Asn^{76}$, $Asn^{77}$, $Ser^{78}$, $Ile^{79}$, $Gly^{80}$, $Val^{81}$, $Thr^{208}$ and $Tyr^{214}$ relative to the amino acid sequence set forth in Table 1. The present invention preferably involves replacement of one or more of the amino acids present in the calcium binding site with a "negatively charged" amino acid such as Asp and Glu, and more preferably Asp. It should be noted that although $Asp^{41}$ in the calcium binding site is a negatively charged amino acid, one embodiment of the present invention involves changing $Asp^{41}$ to $Glu^{41}$. The other embodiments relate to changes other than to $Asp^{41}$.

One preferred embodiment of the present invention involves a subtilisin analog wherein $Asn^{76}$ is converted to $Asp^{76}$. Another embodiment involves conversion of the $Ile^{79}$ to $Asp^{79}$. A preferred embodiment involves a subtilisin analog wherein $Asn^{77}$ is converted to $Asp^{77}$. The more preferred embodiments of the present invention involve the above preferred modifications to the calcium binding site and substitutions of $Asn^{109}$ and $Asn^{218}$ to $Ser^{109}$ and $Ser^{218}$, thus eliminating two unstable Asn-Gly sequences.

In addition to the calcium binding sites described above, subtilisins may have one or more additional calcium binding sites. The claims of the present invention encompass modification of one or more of all calcium binding sites that may be present in the subtilisin. The number of calcium binding sites in any particular subtilisin that may be modified depends on many factors, i.e., the specific subtilisin, the particular application for the subtilisin analog. Other potential calcium binding sites that may be present in subtilisins include the following (1) $Asp^{140}$ and $Pro^{172}$; (2) $Pro^{14}$ and $Gln^{271}$; and (3) $Pro^{172}$ and $Glu^{195}$ or $Asp^{197}$. The specific calcium binding site present in each molecule depends upon the particular subtilisin to be modified. As previously mentioned, the replacement of one or more of the amino acids in the above potential calcium binding sites will result in a subtilisin having improved thermal and pH stability. Representative of replacements include $Asp^{140}$ with $Glu^{140}$, $Pro^{172}$ with $Asp^{172}$, $Pro^{14}$ with $Asp^{14}$, $Gln^{271}$ with $Glu^{271}$, $Glu^{197}$ with $Asp^{197}$.

In addition to modifying the calcium binding sites of a subtilisin molecule, it is preferred to have any Asn-Gly sequence present in the subtilisin deleted or replaced. As previously disclosed in U.S. application Ser. No. 819,241, a conserved sequence, Asn-Gly, at positions 109-110 and especially at positions 218-219 of Bacillus subtilisins has been identified as a major factor responsible for the pH instability of these substances. In order to eliminate the unstable element, $Asn^{218}$-$Gly^{219}$, from the subtilisin molecule it was disclosed to either replace $Asn^{218}$ with any amino acid other than asparagine and/or change $Gly^{219}$ to any amino acid other than glycine. In a like manner, modification of the unstable Asn-Gly element at positions 109-110 was described as providing stability to the analogs described therein.

In addition, as previously noted, a preferred class of analogs of a Bacillus subtilisin according to the present invention have an amino acid sequence wherein in addition to a modification of a calcium binding site, positions comprising an Asn-Gly sequence in the Bacillus subtilisin do not comprise an Asn-Gly sequence in the analog, and in particular wherein there are fewer Asn-Gly sequences than in the Bacillus subtilisin. Most preferably, a position corresponding to position 218 in the amino acid sequence as set forth in Table 1, does not comprise an asparaginyl residue, but rather comprises a residue of a different amino acid, preferably an amino acid selected from among serine, valine, threonine, cysteine, glutamine and isoleucine. To the extent that replacement of asparagine with certain amino acids may give rise to interference with active site conformation, (e.g., due to steric hindrance which may be introduced by the presence of an aromatic amino acid or changes in tertiary structure such as may be introduced by the presence of a proline) substitution with such amino acids would ordinarily be less preferred. Likewise, to the extent that replacement of asparagine with other amino acids may introduce a charged group (e.g., aspartic acid) into the proximity of the active site, such substitution would be less preferred. Illustrative of a presently preferred embodiment is an analog having a modified calcium binding site and a [$Ser^{218}$] modification of the Asn-Gly sequence of the subtilisin. Alternative embodiments of analogs within the contemplation of the invention are those having a modified calcium binding site and wherein $Asn^{109}$ of subtilisin BPN' or of the aprA gene product is replaced, preferably by a serine, and wherein glycine residues at positions 110 and/or 219 are replaced by different amino acid residues. In other subtilisins, modification of a calcium binding site or sites and substitution for Asn at residue 62 or Gly at residue 63 of subtilisins Carlsberg or DY are also comprehended by the present invention.

Due to their capacity to secrete substantial quantities of proteins and because they are currently used to produce detergent proteases, Bacillus micro-organisms represent a preferred host for recombinant production of the subtilisin analogs according to the present invention. Because most Bacilli secrete alkaline and neutral proteases, it is preferable that mutations be introduced into the endogenous alkaline and neutral protease genes of B. subtilis so that the mutated subtilisin may be produced and secreted by B. subtilis in a medium free of other proteases. Thus the present invention also provides mutant strains of B. subtilis which are blocked with respect to the synthesis of endogenous proteases but which retain the ability to synthesize and secrete the subtilisin analogs herein disclosed.

As described in greater detail below, it was found that the pH and thermal stability and the stability in detergent formulations of the subtilisin analogs of the present invention is significantly greater than that of the wild type aprA gene product subtilisin and Carlsberg subtilisin.

A subtilisin analogs according to the invention may be prepared in accordance with the following procedure:

(1) Isolation of the representative subtilisin gene aprA from b. subtilis;

(2) Cloning of the aprA gene on a vector which permits utilization of oligonucleotide site-directed mutagenesis to create desired modifications;

(b 3) Site-directed mutagenesis and sequencing of the resulting DNA to confirm the presence of the desired mutation;

(4) Construction of an expression vector to direct the synthesis of the mutated enzyme in *B. subtilis;*

(5) Construction of mutated *B. subtilis* strains which do not synthesize subtilisin and neutral protease;

(6) Isolation of the enzyme in the extra-cellular growth medium and its purification;

(7) Practice of procedures for insertion of the gene coding for the improved enzyme into the chromosome of a *B. subtilis* strain previously mutated to block synthesis of endogenous proteases.

As used herein, the specific subtilisin analogs are indicated by representing the replaced or deleted amino acid in brackets. For example, a [Ser$^{109}$] subtilisin refers to a subtilisin molecule having a serine in amino acid position 109 and a [Ser$^{109}$, Ser$^{218}$] subtilisin refers to a subtilisin molecule having a serine at amino acid positions 109 and 218.

In Example 1, the aprA gene encoding subtilisin is isolated from the *B. subtilis* genome. In Example 2, the aprA gene is subjected to site-directed mutagenesis. In Example 3, an expression vector containing the mutated aprA gene is constructed. In Example 4, a [Ser$^{109}$] subtilisin analog is prepared. Example 5 describes the preparation of a [Ser$^{109}$, Ser$^{218}$] subtilisin analog. Example 6 describes preparation of a [Asp$^{76}$, Ser$^{109}$, Ser$^{218}$] subtilisin analog. In Example 7, a [Asp$^{76}$, Asp$^{77}$, Ser$^{109}$, Ser$^{218}$] subtilisin analog is prepared. Example 8 describes the preparation of a [Asp$^{76}$, Glu$^{79}$, Ser$^{109}$, Ser$^{218}$] subtilisin analog. In Example 9, two mutant strains of *B. subtilis* which produce no detectable extra-cellular proteases are constructed. Example 10 describes procedures for integration of a mutated aprA gene into the chromosome of B. subtilis. In Example 11 wild-type and mutant aprA subtilisins are isolated and purified. Examples 12 through 14 compare the thermostability of [Ser$^{218}$] subtilisin to that of wild-type aprA gene product.

In addition to a subtilisin analog of the present invention, detergent compositions of the present invention may comprise:

(a) At least one surfactant which may be anionic, non-ionic, or amphoteric, or a water-soluble soap. Typically, an anionic surfactant (e.g., a linear alkyl aryl sulphonate) is used in admixture with a nonionic (e.g., an alkyl phenyl polyglycol ether) in amounts of 5–30 and 1–5 percent by weight, respectively, of the detergent composition.

(b) One or more builders, preferably having a concomitant sequestering function. Sodium tripolyphosphate, sodium citrate, sodium silicate, and zeolites are examples of such compounds, usually constituting from 10 to 70 percent by weight of the detergent composition.

(c) A bleaching agent, preferably a peroxy compound such as sodium perborate, typically incorporated in an amount up to 30 percent by weight of the composition.

(d) Ancillary agents, such as carboxymethyl cellulose, optical brighteners and perfumes. If required, a pH-adjusting agent is added to give a pH of the laundering medium in the range of from 8.0 to 10.5.

The detergent compositions contain an effective amount of one or more of the subtilisin analogs of the present invention. As used herein "effective amount of a subtilisin analog" refers to the quantity of subtilisin analog necessary to achieve the enzymatic activity necessary in the specific detergent composition. Such effective amounts are readily ascertained by one of ordinary skill in the art and is based on many factors, such as the particular subtilisin analog utilized, the cleaning application, the specific composition of the detergent composition, whether a liquid or dry composition is required and the like.

The particulate subtilisin analog preparation of the invention is added in an amount calculated to give an enzyme activity of at least 0.1 Anson units (AU, vide infra), preferably 0.5–2.5 AU per 100 g of detergent composition. If required, balance to 100 percent may be established with an inorganic filler, preferably sodium sulphate.

Liquid detergent compositions may be prepared from enzyme slurries, preferably in non-aqueous media. Typically, such slurries may consist of a suspension of finely ground subtilisin analog concentrate in a liquid non-ionic surfactant, for example Tergitol 15 S 9 or a mixture of such surfactants. Usually, the slurry will also contain one or more inorganic fillers, such as finely ground sodium chloride, optionally in admixture with a suspension stabilizer, for example fumed silica (Aerosil 200). Tergitol and Aerosil are trademarks.

A subtilisin analog of the invention is added in an amount calculated to give a protease activity of at least 0.1 AU preferably 0.5–2.5 AU per 100 g of liquid detergent composition.

The detergent compositions may be prepared in the usual manner, for example by mixing together the components. Alternatively, a pre-mix is made, which is then mixed with the remaining ingredients.

Because of the good stability and activity properties described, the subtilisin analogs according to the invention can be used in all fields where proteolytic enzymes are generally used. In particular, it can be used for detergents and cleansers or spot removers, as a depilatory in tanning, and also in the food industry for the preparation of protein hydrolysates and in serology for the detection of incomplete antibodies. It is particularly advantageous for use in the food industry and in serology that the subtilisin analogs according to the invention have excellent stability in the solid or dissolved form that physiologically acceptable quantities of calcium ions may not be necessary to stabilize the subtilisin analog in aqueous solutions, in contrast to those of other enzyme preparations.

The following Examples will further serve to illustrate the invention although it will be understood that the invention is not limited to these specific examples.

Example 1

*B. subtilis* strain QB127 (trpC2 leuA8 sacU$^h$200) [Lepesant, et al., *Molec. Gen. Genet.*, 118, 135–160 (1982)] was obtained from the Bacillus Genetic Stock Center at the Ohio State University, Columbus, Ohio. This strain overproduces extracellular serine and metal proteases, α-amylase and levansucrase relative to isogenic sacU+ strains due to the pleiotropic effect of the sacU$^h$200 mutation [Lepesant, et al., in Schlessinger, D., ed., *Microbiology*, 1976, American Society for Microbiology, Washington, D.C., p. 65 (1976)]. Thus, strain QB127 is a suitable source of DNA for isolating the aprA gene which codes for subtilisin.

Genomic DNA was isolated from cells of *B. subtilis* strains QB127 in accordance with the procedure of Saito, et al., *Biochim. Biophys. Acta.* 72, 619–629 (1963). Purified chromosomal DNA was digested to completion with the EcoRI restriction endonuclease.

The resulting DNA fragments were resolved on a low-melting point agarose gel by electrophoresis and fragments in the 4.4 to 8.0 kilobase (kb) range were isolated. These fragments were ligated to pCFM936 (A.T.C.C. No. 53,413 from the American Type Culture Collection, 1230 Parklawn Drive, Rockville, Maryland) an *Escherichia coli* (*E. coli*) plasmid which displays higher copy numbers at elevated temperatures and which confers kanamycin resistance. The vector was digested with EcoRI and dephosphorylated with calf intestine alkaline phoshpatase prior to ligation.

The ligation products were introduced into *E. coli* C600 (A.T.C.C. No. 23,724 from the American Type Culture Collection, 12301 Parklawn Drive, Rockville, Maryland) and following overnight incubation on L-agar supplemented with 10 μg/ml kanamycin, kanamycin-resistant host cells were selected. Plasmid DNA was amplified by incubating the selected host cells at 42° C. for 4 hours. Colonies were then transferred to nitrocellulose filters and processed in accordance with a colony hybridization procedure described by Grunstein, et al., *Proc. Natl. Acad. Sci. (USA)*, 72, 3961 (1975), An oligonucleotide probe was used to screen for colonies which harbored the subtilisin gene on pCFM936. The probe synthesized by the phosphite method described by Beaucage, et al., *Tetrahedron Letters*, 22, 1859–1862 (1981) had the nucleotide sequence

5′ GCGCAATCTGTTCCTTATGGC 3′ which corresponds to the amino-terminus of the aprA gene produce (Wong, et al., Proc. Natl. Acad. Sci. (*USA*), 81, 1184–1188 (1984); Stahl, et al., *J. Bacteriol.*, 158, 411–418 (1984). A hybridization temperature of 55° C. was employed and 5 positive colonies were identified out of a total of 400. The plasmid DNA from one of the positive colonies was designated pCFM936 apr2.

Plasmid pCFM936 apr2 was digested with EcoRI alone, with HindIII alone and with EcoRI and HindIII in combination. Sizes of EcoRI fragments of the subtilisin gene conformed to those described in Stahl, et al., supra, but several otherwise undescribed HindIII sites were discovered. As described herein in Example 3, two of the HindIII sites were utilized in the genetic manipulations of the subtilisin gene.

Figure 2:
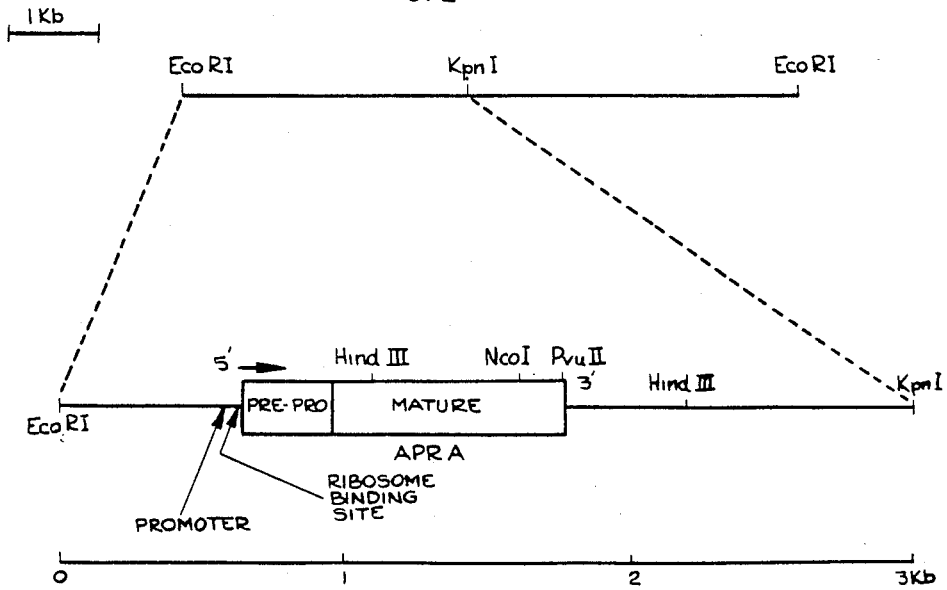
FIG. 2 is a partial restriction map of an aprA gene-containing an EcoRI-KpnI gene fragment of *Bacillus subtilis* (*B. subtilis*) strain QB127 and includes a partial restriction map of the aprA gene and flanking sequences.

It was determined that a large 6.5 kb EcoRI fragment of *B. subtilis* QB127 genomic DNA carried the aprA gene, its regulatory sequences and unrelated flanking sequences by verifying that restriction enzyme digests conformed to the results reported by Stahl, et al., supra. This was confirmed by DNA sequencing using the dideoxy chain termination method described by Sanger, et al., *J. Mol. Biol.*, 143, 161–178 (1980). A 3.0 kb EcoRI to KpnI subfragment of the 6.5 kb EcoRI fragment, as illustrated in FIG. 2, was also found to contain the aprA gene, its regulatory sequences, and unrelated flanking sequences. Although the KpnI-EcoRI fragment is reported to be 2.5 kb in length by Stahl, et al., and in the legend to FIG. 1 therein, comparison of the scale of FIG. 1 and the scaled depiction of the fragment therein reveal that, even in Stahl, et al., the KpnI-EcoRI fragment is substantially larger than 2.5 kb.

A cloning vector for Bacillus host systems, plasmid pAMB11, was constructed as follows. The plasmid pTG402 (Northern Regional Research Laboratories, United States Department of Agriculture, Peoria, Illinois, strain number NRRL B-15264) was partially digested with the RsaI restriction endonuclease. Fragments were ligated to M13 mp18 (available from Bethesda Research Laboratories, Gaithersburg, Maryland as catalog number 8227SA) which had been previously digested with HincII. Ligation products were introduced into *E. coli* JM103 (available from Pharmacia, Inc., Piscataway, New Jersey as catalog number 27-1545-01) by transformation in accordance with the procedure of Mandel, et al., *J. Mol. Biol.*, 53, 154, (1970). Bacteriophage plaques were sprayed with 0.5M catechol (prepared in distilled water) to detect the functional expression of an xylE gene derived from pTG402. The xylE gene encodes catechol 2,3-dioxygenase and is useful for detecting promoters in a variety of organisms [Zukowski, et al., *Proc. Natl. Acad. Sci. (USA)*, 80, 1101–1105 (1983)].

The xylE gene was then transferred as a 1.0 kb EcoRI to PstI fragment to the *E. coli/B. subtilis* plasmid pHV33 (available from the American Type Culture Collection as A.T.C.C. 39217) [Primrose, et al. *Plasmid*, 6, 193–201 (1981)] obtained from R. Dedonder (Institut Pasteur, Paris, France). The pHV33 plasmid had been previously digested with EcoRI and PstI so that the xylE-containing fragment, when ligated in this region, would inactivate a gene for ampicillin resistance. The resulting plasmid, pAMB21, contains a functional xylE gene in *E. coli* host cells, but requires the addition of a promoter for xylE to be expressed in *B. subtilis* host cells. *E. coli* cells harboring pAMB21 are resistant to tetracycline (15 μg/ml) and chloramphenicol (20 μg/ml) while *B. subtilis* cells harboring pAMB21 are resistant only to chloramphenicol (5 μg/ml).

The $t_{oop}$ transcription termination sequence of bacteriophage lambda was transferred from plasmid pCFM936 (on a 400 base pair PstI to BglII fragment) to the unique PstI site of pAMB21. A synthetic nucleotide with the sequence, 5′ GATCTGCA 3′, was constructed to join the BglII extremity of the $t_{oop}$ fragment to the PstI site of the vector pAMB21. The resulting plasmid was designated pAMB22 and had properties identical to pAMB21 except for the inclusion of a transcription terminator. The pAMB22 plasmid is useful for detecting strong promoters that are functional in *B. subtilis*.

Figure 3:
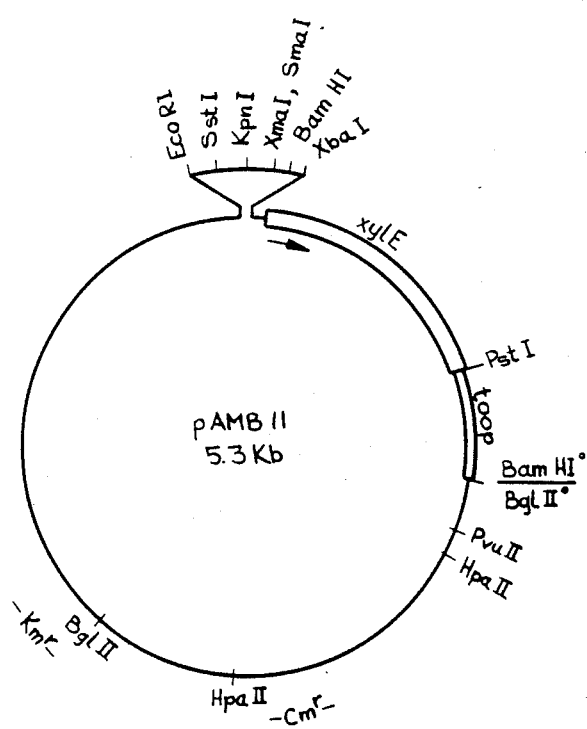
FIG. 3 is a partial restriction map of a plasmid pAMB11.

The 1.4 kb EcoRI to BglII fragment of DNA from pAMB22 that contains xylE and $t_{oop}$ was isolated from a low-melting point agarose gel after electrophoresis of restricted fragments. The 1.4 kb piece of DNA was ligated to plasmid pBD64 (available from Bacillus Genetic Stock Center, number 1E22) which had been previously digested with EcoRI and BamHI. The resulting 5.3 kb plasmid, pAMB11, contains the polylinker sequence of M13mp18 (EcoRI, SstI, XmaI, Sma, BamHI and XbaI) upstream of the xylE gene which is followed by $t_{oop}$, as shown in FIG. 3. The pAMB11 plasmid is capable of replicating in *B. subtilis* and confers upon host cells resistance to chloramphenicol (5 μg/ml) and/or kanamycin (5 μg/ml).

Figure 4:
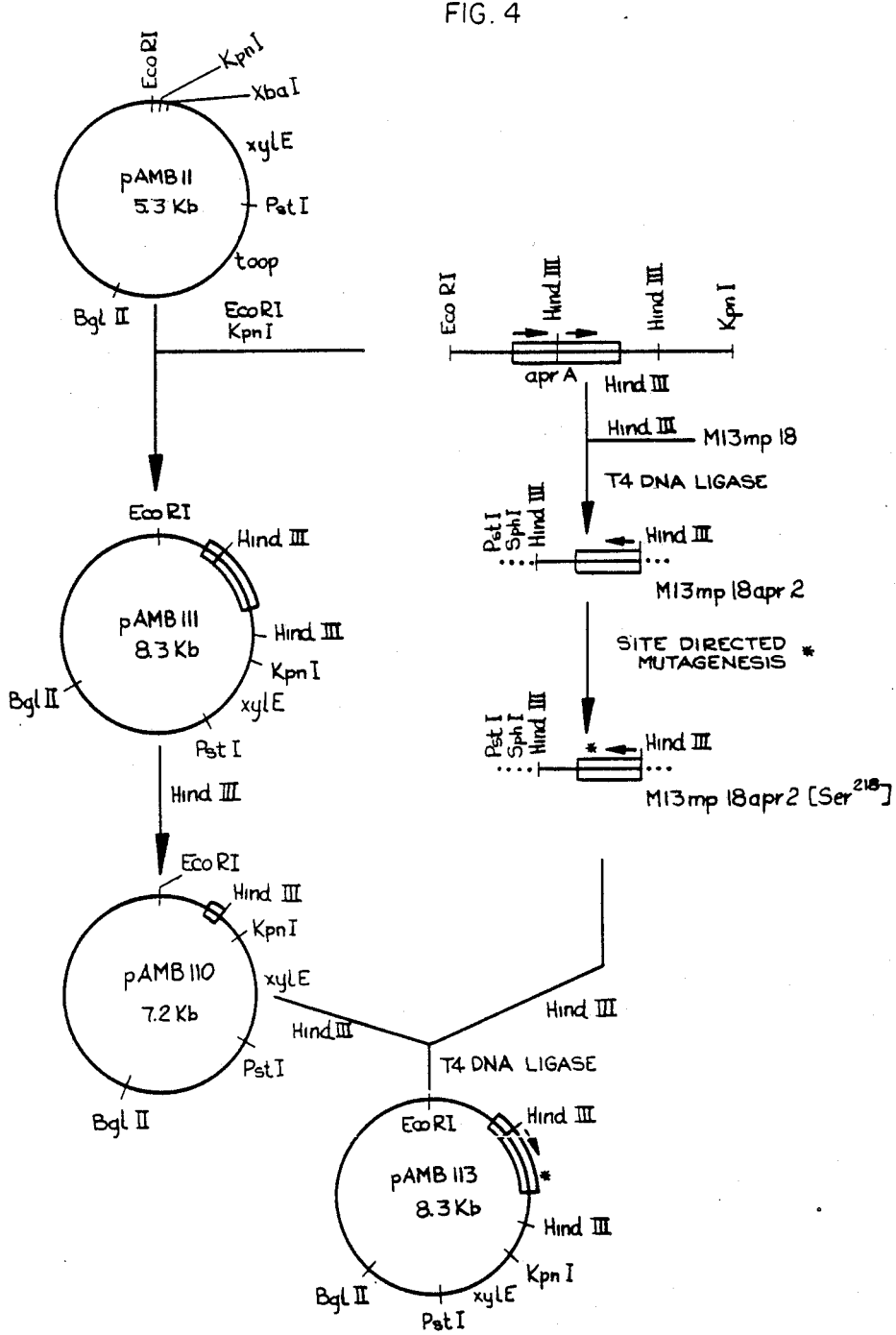
FIG. 4 is a flowchart illustrating stages in construction of pAMB113, a plasmid which directs synthesis of $[Ser]^{218}$-subtilisin from *B. subtilis* host cells.

As illustrated in FIG. 4, the purified EcoRI to KpnI fragment containing aprA was cloned onto pAMB11 to form pAMB111. Ligation products were introduced into *B. subtilis* MI112 (arg-15 leuB thr5 recE4) (available from Bacillus Genetic Stock Center as No. 1A423) by the protoplast transformation method described by Chang, et al., *Mol. Gen. Genet.*, 168, 111–115 (1979). *B.* subtilis MI112 without plasmid DNA is protease-proficient (Prt+ phenotype), but secreted levels of subtilisin are rather low. Chloramphenicol-resistant (Cm') transformants were transferred onto L-agar plates supplemented with 1.5% (w/v) skim milk and 5 μg/ml chloramphenicol, then incubated at 37° C.

After incubation at 37° C. for approximately sixteen hours, colonies of MI112 harboring plasmid pAMB111 produced a clear halo surrounding each colony. Halos were formed by the proteolytic action of subtilisin on the casein component of the skim milk medium supplement. MI112 harboring the pAMB11 vector alone had no visible halo after 16 hrs. of incubation, although a slight halo eventually developed after 40 hrs. of incubation at 37° C. Cells carrying pAMB111 were clearly distinguished from cells carrying pAMB11 by a difference in halo size. The cloning of the aprA gene is a fully functional form thus led to a high level production and secretion of subtilisin by *B. subtilis*.

EXAMPLE 2

As illustrated in FIG. 4, a 3.0 kb EcoRI to KpnI genomic fragment, the isolation of which is described in Example 1, was digested with HindIII to produce three fragments: (1) a 1.1 kb EcoRI to HindIII fragment carrying genetic regulatory sequences for aprA gene expression, the "pre-pro" region of the gene required for extracellular export of subtilisin, and the DNA sequence coding for the first 49 amino acids of mature subtilisin; (2) a 1.1 kb HindIII to HindIII fragment carrying DNA sequences coding for amino acids 50 through 275 (carboxy-terminus) of subtilisin along with a transcription termination sequence and 3' non-coding sequences; and (3) a 0.8 kb HindIII to KpnI fragment containing 3' non-coding sequences.

The 1.1 kb fragment flanked by HindIII sites was cloned to the single HindIII site of bacteriophage M13 mp18 for the purposes of DNA sequencing and site-directed mutagenesis. One of the recombinants, designated M13 mp18 apr2, provided single stranded template DNA required for site-directed mutagenesis of the aprA gene.

The coding region of the aprA gene was sequenced and the results of the sequence are set forth in Table 1 herein. It should be noted that the specific identity of the initial 5 codons of the leader region is attributable to the report of Stahl, et al., supra, and Wong, et al., supra, of sequence information for the aprA gene, and that there exist codon sequence differences from Stahl, et al., supra, at amino acid positions 84 and 85. Specifically, Stahl, et al., supra, reports a codon GTT (coding for valine) at amino acid position 84 while the codon GTA (also coding for valine) appears in Table 1. Stahl, et al., supra, also reports a codon AGC (coding for serine at amino acid position 85 as opposed to the codon GCG (coding for alanine) in Table 1.

TABLE 1

−105
Met Arg Ser Lys Lys Leu Trp Ile Ser Leu Leu
GTG AGA AGC AAA AAA TTG TGG ATC AGC TTG TTG

Phe Ala Leu Thr Leu Ile Phe Thr Met Ala Phe
TTT GCG TTA ACG TTA ATC TTT ACG ATG GCG TTC

Ser Asn Met Ser Ala Gln Ala Ala Gly Lys
AGC AAC ATG TCT GCG CAG GCT GCC GGA AAA

Ser Ser Thr Glu Lys Lys Tyr Ile Val Gly Phe
AGC AGT ACA GAA AAG AAA TAC ATT GTC GGA TTT

TABLE 1-continued

Lys Gln Thr Met Ser Ala Met Ser Ser Ala Lys
AAA CAG ACA ATG AGT GCC ATG AGT TCC GCC AAG

Lys Lys Asp Val Ile Ser Glu Lys Gly Gly Lys
AAA AAG GAT GTT ATT TCT GAA AAA GGC GGA AAG

Val Gln Lys Gln Phe Lys Tyr Val Asn Ala Ala
GTT CAA AAG CAA TTT AAG TAT GTT AAC GCG GCC

Ala Ala Thr Leu Asp Glu Lys Ala Val Lys
GCA GCA ACA TTG GAT GAA AAA GCT GTA AAA

Glu Leu Lys Lys Asp Pro Ser Val Ala Tyr Val
GAA TTG AAA AAA GAT CCG AGC GTT GCA TAT GTG

−1 +1
Glu Glu Asp His Ile Ala His Glu Tyr Ala Gln
GAA GAA GAT CAT ATT GCA CAT GAA TAT GCG CAA

10
Ser Val Pro Tyr Gly Ile Ser Gln Ile Lys Ala
TCT GTT CCT TAT GGC ATT TCT CAA ATT AAA GCG

20
Pro Ala Leu His Ser Gln Gly Tyr Thr Gly Ser
CCG GCT CTT CAC TCT CAA GGC TAC ACA GGC TCT

30
Asn Val Lys Val Ala Val Ile Asp Ser Gly Ile
AAC GTA AAA GTA GCT GTT ATC GAC AGC GGA ATT

40
Asp Ser Ser His Pro Asp Leu Asn Val Arg Gly
GAC TCT TCT CAT CCT GAC TTA AAC GTC AGA GGC

50
Gly Ala Ser Phe Val Pro Ser Glu Thr Asn Pro
GGA GCA AGC TTC GTA CCT TCT GAA ACA AAC CCA

60
Tyr Gln Asp Gly Ser Ser His Gly Thr His Val
TAC CAG GAC GGC AGT TCT CAC GGT ACG CAT GTA

70
Ala Gly Thr Ile Ala Ala Leu Asn Asn Ser Ile
GCC GGT ACG ATT GCC GCT CTT AAT AAC TCA ATC 80                                              90
Gly Val Leu Gly Val Ala Pro Ser Ala Ser Leu
GGT GTT CTG GGC GTA GCG CCA AGC GCA TCA TTA

100
Tyr Ala Val Lys Val Leu Asp Ser Thr Gly Ser
TAT GCA GTA AAA GTG CTT GAT TCA ACA GGA AGC

110
Gly Gln Tyr Ser Trp Ile Ile Asn Gly Ile Glu
GGC CAA TAT AGC TGG ATT ATT AAC GGC ATT GAG

120
Trp Ala Ile Ser Asn Asn Met Asp Val Ile Asn
TGG GCC ATT TCC AAC AAT ATG GAT GTT ATC AAC

130
Met Ser Leu Gly Gly Pro Thr Gly Ser Thr Ala
ATG AGC CTT GGC GGA CCT ACT GGT TCT ACA GCG

140
Leu Lys Thr Val Val Asp Lys Ala Val Ser Ser
CTG AAA ACA GTC GTT GAC AAA GCC GTT TCC AGC

150
Gly Ile Val Val Ala Ala Ala Ala Gly Asn Glu
GGT ATC GTC GTT GCT GCC GCA GCC GGA AAC GAA

160
Gly Ser Ser Gly Ser Thr Ser Thr Val Gly Tyr
GGT TCA TCC GGA AGC ACA AGC ACA GTC GGC TAC

TABLE 1-continued

```
        170
Pro Ala Lys Tyr Pro Ser Thr Ile Ala Val Gly
CCT GCA AAA TAT CCT TCT ACT ATT GCA GTA GGT

180
Ala Val Asn Ser Ser Asn Gln Arg Ala Ser Phe
GCG GTA AAC AGC AGC AAC CAA AGA GCT TCA TTC 190                    200
Ser Ser Ala Gly Ser Glu Leu Asp Val Met Ala
TCC AGC GCA GGT TCT GAG CTT GAT GTG ATG GCT

210
Pro Gly Val Ser Ile Gln Ser Thr Leu Pro Gly
CCT GGC GTG TCC ATC CAA AGC ACA CTT CCT GGA

220
Gly Thr Tyr Gly Ala Tyr Asn Gly Thr Ser Met
GGC ACT TAC GGC GCT TAT AAC GGA ACG TCC ATG

230
Ala Thr Pro His Val Ala Gly Ala Ala Ala Leu
GCG ACT CCT CAC GTT GCC GGA GCA GCA GCG TTA

240
Ile Leu Ser Lys His Pro Thr Trp Thr Asn Ala
ATT CTT TCT AAG CAC CCG ACT TGG ACA AAC GCG

250
Gln Val Arg Asp Arg Leu Glu Ser Thr Ala Thr
CAA GTC CGT GAT CGT TTA GAA AGC ACT GCA ACA

260
Tyr Leu Gly Asn Ser Phe Tyr Tyr Gly Lys Gly
TAT CTT GGA AAC TCT TTC TAC TAT GGA AAA GGG 270                   275
Leu Ile Asn Val Gln Ala Ala Ala Gln OC
TTA ATC AAC GTA CAA GCA GCT GCA CAA TAA TAG

TAAAAAGAAGCAGGTTCCTCCATACCTGCTTCTTTTTA

TTTGTCAGCATCCTGATGTTCCGGCGCATTCTC
```

Bacteriophage M13 mp18 apr2 was constructed by inserting a 1.1 kb HindIII to HindIII fragment of *B. subtilis* QB127 genomic DNA, carrying nucleotide sequences coding for amino acids 50 through 275 (carboxyl-terminus) of aprA-subtilisin along with a transcription termination sequence and 3' non-coding sequences, in the unique HindIII site of bacteriophage M13 mp18. To eliminate the 3' non-coding sequences, a KpnI restriction endonuclease site was introduced, by site-directed mutagenesis, at a position immediately following the transcription termination sequence.

Site-directed mutagenesis was conducted in accordance with a procedure described by Norrander et. al., *Gene*, 26, 101-106 (1983). Single-stranded DNA from M13 mp18 apr2 was annealed to a primer,

```
          *   *
5' TCCTGAGGTACCGGCGCATTC 3'
``` which was synthesized by the phosphite method described by Beaucage et. al., *Tetrahedron Letters* 22, 1859-1862 this region except for two (marked by asterisks), where a thymine (T) was changed to gaunine (G) and another thymine (T) was changed to adenine (A), thus creating a KpnI site (underlined) in this region.

The primer was annealed to M13 mp18 apr2 DNA at 65° C. and the annealed DNA was slowly cooled to approximately 22° C. and then polymerized for 2 hrs. at 15° C. in a reaction mixture which consisted of 12.5 μl of annealed DNA solution, 2.5 μl of 10 mM each of dATP, dCTP and dGTP, 20 μl of 12 mM ATP, 0.1 μl Klenox DNA polymerase, 0.1 μl T4 DNA ligase and 13 μl sterile distilled water. The resulting double-stranded, covalently closed circular DNA was introduced into *E. coli* JM103 by transfection.

Bacteriophage plaques were then transferred to Gene Screen ™ (New England Nuclear, Beverly, Massachusetts) hybridization membranes. Plaques which contained DNA with the desired base changes were identified by hybridization to the radioactively labeled ($\lambda-^{32}p$) synthetic oligonucleotide used for the mutagenic priming reaction described above. Hybridization was performed at a restrictive temperature (65° C.) in order that only DNA carrying a KpnI mutation would hybridize to the synthetic oligonucleotide. The presence of the KpnI mutation downstream of the aprA gene on DNA from a single purified plaque, designated M13 mp18 apr2 KpnI, was confirmed by DNA sequencing by the procedure described by Sanger et. al., supra and restriction enzyme analysis.

Figure 7:
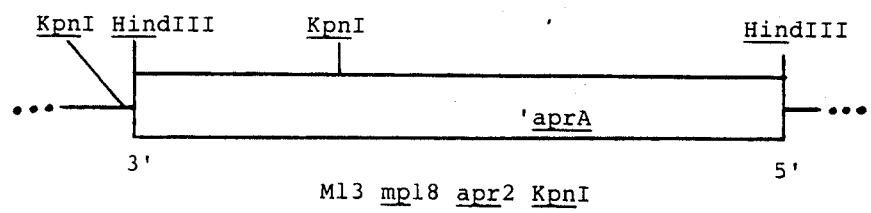
FIG. 7 illustrates the construction of M13 mp18 apr4.
Figure 7:
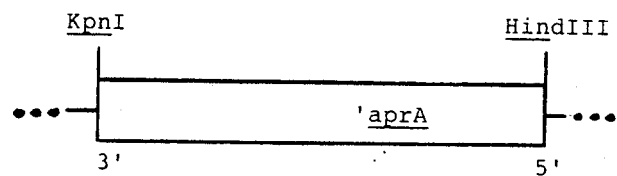

A 1.1 kb segment carrying most of the 3' non-coding region was deleted by digesting M13 mp18 apr2 KpnI with KpnI, religating digestion products at a concentration of 500 ng DNA/ml, then introducing the ligation products into *E. coli* JM103 by transfection. Bacteriophage plaques which contained DNA with the desired 0.35 kb deletion were identified by restriction endonuclease analysis. Bacteriophage from one such plaque was designated M13 mp18 apr4 (FIG. 7). M13 mp18 apr4 provided single-stranded template DNA for site-directed mutagenesis of the aprA gene described hereinafter in Example 3.

EXAMPLE 3

In order to express mutated subtilisin genes in *B. subtilis*, the plasmid pAMB106 was constructed as a vehicle for the mutated gene, as follows:

(1) pAMB111 was digested with HindIII. A 1.1 kb segment carrying most of the aprA gene was deleted by re-ligating HindIII digestion products of pAMB111 at a concentration of approximately 1 μg/ml. This resulted in the formation of pAMB110 as illustrated in FIG. 4. The pAMB110 plasmid carries genetic regulatory sequences for expression of the subtilisin gene, the "prepro" region required for secretion of subtilisin, and the DNA sequence coding for the 3' non-coding region of mature subtilisin and the first 49 amino acids of mature subtilisin.

(2) Plasmid pAMB110 was digested with BamHI and PstI in combination. This produced DNA fragments of two sizes, 6.2 kb and 1.0 kb. The 1.0 kb fragment carries the xylE gene, coding for catechol 2,3-dioxygenase, from the TOL plasmid of Pseudomonas putida mt-2 (Zukowski et. al., supra).

(3) The larger, 6.2 kb —BamHI—PstI fragment was self-ligated with the aid of a single-stranded synthetic oligonucleotide, 5' GATCTGCA 3', which was synthesized by the phosphite method described by Beaucage et. al., supra, and T4 DNA ligase. Ligation products were introduced into *B. subtilis* MI112 (arg-15 leuB thr5 recE4 (available from Bacillus Genetic Stock Center as No. 1A423) by the protoplast transformation method described by Change et. al., *Mol. Gen. Genet.* 168, 111-115 (1979).

Figure 6:
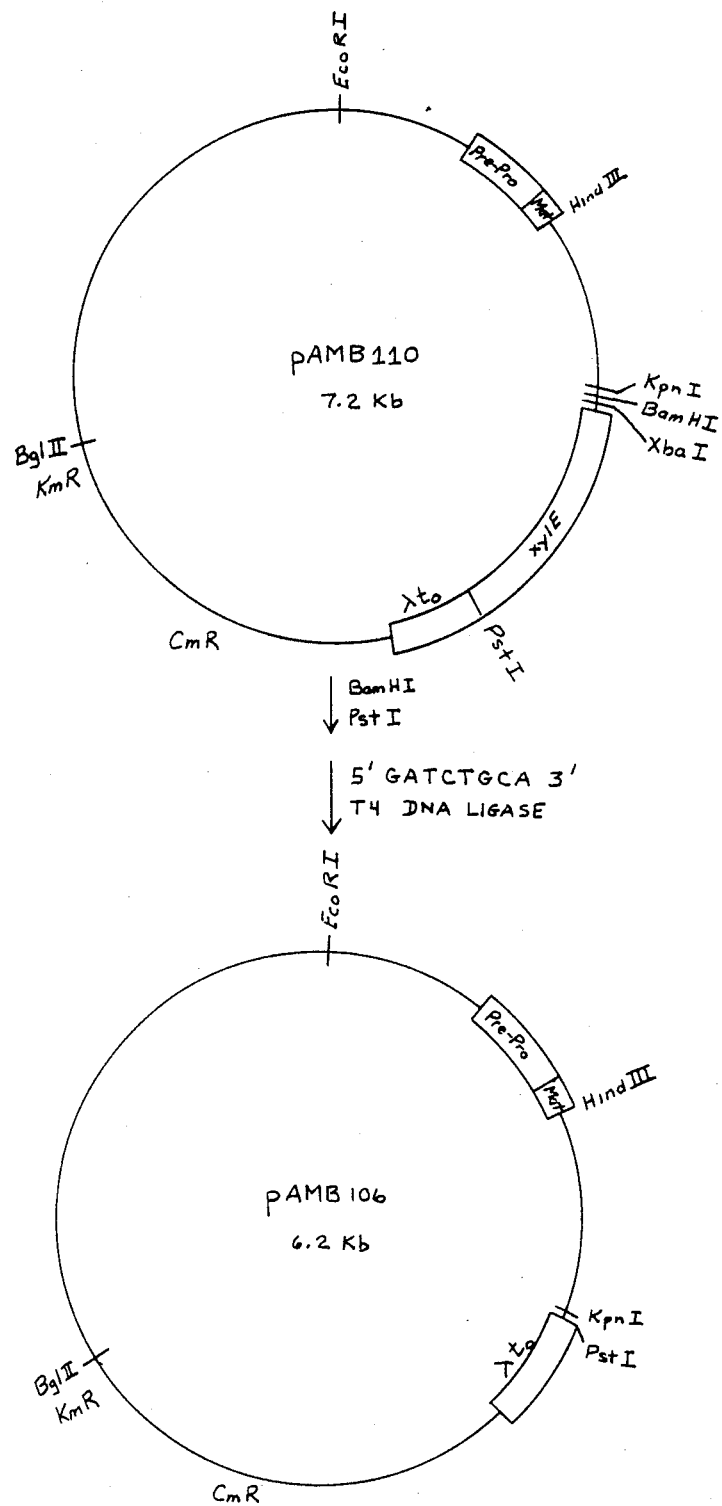
FIG. 6 illustrates the construction of pAMB106.

Chloramphenicol-resistant ($CM^R$) colonies were screened for plasmid content. The 6.2 kb plasmid pAMB106 was identified by restriction endonuclease analysis. It is identical to plasmid pAMB110 except that xylE has been deleted (FIG. 6).

Because it is lacking DNA coding for amino acids 50 through 275 of aprA subtilisin, pAMB106 does not synthesize subtilisin when introduced into *B. subtilis* host cells. Subtilisin is synthesized only after insertion of the remainder of the subtilisin gene, i.e., either the native DNA sequence or an analog-encoding sequence.

EXAMPLE 4

Preparation of a [Serine$^{109}$] Subtilisin Analog

Single-stranded DNA from bacteriophage M13mp18 apr4 was annealed to a primer,

```
                        *
5' TGG ATT ATT AGC GGC ATT GAG TGG 3'
    106 107 108 109 110 111 112 113
    TRP ILE ILE SER GLY ILE GLU TRP
``` which was synthesized by the phosphite method described by Beaucage et. al., supra. The primer was homologous to the nucleotides comprising codons for amino acids 106 through 113 of aprA-subtilisin except for one base change (marked by an asterisk) where an A was changed to a G to allow for the transition which would change Asn$^{109}$ (codon AAC) to Ser$^{109}$(codon AGC).

The primer was annealed to M13mp18 apr4 DNA at 65° C. and the annealed DNA was slowly cooled to approximately 22° C. and then polymerized, ligated and transfected as described in Example 2.

Bacteriophage plaques were transferred to hybridization membranes, then those which contained DNA with the desired base change were identified by hybridization to a radioactively labeled ($\alpha-^{32}p$) oligonucleotide used for the mutagenic priming reaction described above. Hybridization was performed at 65° C. One positive plaque contained bacteriophage designated as M13mp18 apr4 [Ser$^{109}$]. Double-stranded DNA from this bacteriophage was digested with HindIII and KpnI in combination, then the 750 bp fragment carrying the mutated portion of the aprA-subtilisin gene was ligated to pAMB106 which had been previously digested with HindIII and KPnI. The resulting plasmid, pAMB129, may be introduced into a suitable *B. subtilis* host cells for synthesis and secretion of [Ser$^{109}$]-subtilisin.

EXAMPLE 5

Preparation of a [Serine 109, Serine 218] Subtilisin Analog

Single-stranded DNA from M13mp18 apr4 [Ser$^{109}$] was annealed to a primer:

```
                  *
5' GGC GCT TAT AGC GGA AC 3'
   215 216 217 218 219 220
   GLY ALA TYR SER GLY THR
``` which was synthesized by the phosphite method described by Beuacage et. al., supra. The primer was homologous to nucleotides comprising codon for amino acids 215 through 220 of aprA-subtilisin except for one base change (marked by an asterisk) where an A was changed to a G to allow for the transition which would change Asn$^{218}$ (codon AAC) to Ser$^{218}$ (codon AGC). The conditions for annealing, polymerization, ligation, transfection, and identification of positive plaques were as described in Example 2. A single purified plaque contained bacteriophage designed as M13mp18apr4 [Ser$^{109}$, Ser$^{218}$]. Double-stranded DNA from this bacteriophage was digested with HindIII and KpnI in combination, then a 750 bp fragment carrying the two mutations was ligated to pAMB106 which had been previously digested with HindIII and KpnI. The resulting plasmid, pAMB130, may be introduced into *B. subtilis* host cells for synthesis and sceretion of [Ser$^{109}$, Ser$^{218}$]-subtilisin.

EXAMPLE 6

Preparation of a [Asp 76, Ser 109, Ser 218 ] Subtilisin Analog

Single-stranded DNA from M13mp18 apr4 [Ser$^{109}$, Ser$^{218}$] was annealed to a primer:

```
                *
5' GCT CTT GAT AAC TCA ATC 3'
   74  75  76  77  78  79
   ALA LEU ASP ASN SER ILE
``` which was synthesized by the phosphite method described by Beaucage et. al., supra. The primer was homologous to the nucleotides comprising codons for amino acids 74 through 79 of aprA-subtilisin except for one base change (marked by an asterisk), where an A was changed to a G to allow for the transition which would change Asn$^{76}$ (codon AAT) to Asp$^{76}$ (codon GAT).

The primer was annealed to M13mp18 [Ser$^{109}$, Ser$^{218}$] DNA at 65° C. and the annealed DNA was slowly cooled to approximately 22° C. and polymerized, ligated and transfected as described in Example 2.

Bacteriophage plaques were transferred to hybridization membranes and those which contained DNA with the desired base change were identified by hybridization as described in Example 2 except that hybridization was performed at 46° C. One positive plaque contained bacteriophage designated at M13mp18 apr4 [Asp$^{76}$, Ser$^{109}$, Ser$^{218}$]. Double-stranded DNA from the bacteriophage was digested with HindIII and KpnI in combination, then a 750 bp fragment carrying the three mutations of the aprA-subtilisin gene was ligated to pAMB106 which had been previously digested with HindIII and KpnI. The resulting plasmid, pAMB131, may be introduced into *B. subtilis* host cells for synthesis and secretion of [Asp$^{76}$, Ser$^{109}$, Ser$^{218}$]-subtilisin.

EXAMPLE 7

Preparation of a [Asp$^{76}$, Asp$^{77}$, Ser$^{109}$, Ser$^{218}$] Subtilisin Analog Single-stranded DNA from M13mp18 apr4 [Asp$^{76}$, Ser$^{109}$, Ser$^{218}$] was annealed to a primer:

```
                *   *
5' GCT CTT GAT GAT TCA ATC CGT 3'
   74  75  76  77  78  79  80
   ALA LEU ASP ASP SER ILE GLY
``` which was synthesized by the phosphite method described by Beaucage et. al., supra. The primer was homologous to the nucleotides comprising codons for amino acids 74 through 80 of [Asp$^{76}$, Ser$^{109}$, Ser$^{218}$]-subtilisin except for two base changes (marked by asterisks), where an A changed to a G and a C was changed to a T for the transitions which changed Asn$^{77}$ (codon AAC) to Asp$^{77}$ (codon GAT).

The primer was annealed to M13mp18 apr4 [Asp$^{76}$, Ser$^{109}$, Ser$^{218}$] DNA at 65° C. and the annealed DNA was slowly cooled to approximately 22° C. and polymerized, ligated and transfected as described in Example 2.

Bacteriophage plaques were transferred to hybridization membranes and those which contained DNA with the desired base changes were identified by hybridization as described in Example 2 except that hybridization was conducted at 45° C. One positive plaque contained bacteriophage designated as M13mp18 apr4 [Asp$^{76}$, Asp$^{77}$, Ser$^{109}$, Ser$^{218}$]. Double-stranded DNA from this bacteriophage was digested with HindIII and KpnI in combination, then the 750 bp fragment carrying the four mutations of the aprA-subtilisin gene was ligated to pAMB106 which had been previously digested with HindIII and KpnI. The resulting plasmid, pAMB132, may be introduced into B. subtilis host cells for synthesis and secretion of [Asp$^{76}$, Asp$^{77}$, Ser$^{109}$, Ser$^{218}$]-subtilisin.

EXAMPLE 8

Preparation of a [Asp$^{76}$, Glu$^{79}$, Ser$^{109}$, Ser$^{218}$] Subtilisin Analog Single-stranded DNA from M13mp18 apr4 [Asp$^{76}$, Ser$^{109}$, Ser$^{218}$] was annealed to a primer:

```
              *  *   *
5' T GAT AAC TCA GAA GGT GTT CTG G 3'
   75 76  77  78  79  80  81  82 83
      ASP ASN SER GLU GLY VAL LEU
``` which was synthesized by the phosphite method described by Beaucage et. al., supra. The primer was homologous to the nucleotides comprising partial codons for amino acids 75 and 83 and entire codons for amino acids 76 through 82 of [Asp$^{76}$, Ser$^{109}$, Ser$^{218}$]-subtilisin except for three base changes (marked by asterisks), wherein an A was changed to a G, a T was changed to an A, and a C was changed to an A, which changed Ile$^{79}$ (codon ATC) to Glu$^{79}$ (codon GAA).

The primer was annealed to M13mp18 apr4 [Asp$^{76}$, Ser$^{109}$, Ser$^{218}$] DNA at 65° C. and the annealed DNA was slowly cooled to approximately 22° C. and was polymerized, ligated and transfected as described in Example 2.

Bacteriophage plaques were transferred to hybridization membranes and those which contained the desired base changes were identified by hybridization as described in Example 2 except that hybridization was performed at 45° C. One positive plaque contained bacteriophage designated as M13mp18 apr4 [Asp$^{76}$, Glu$^{79}$, Ser$^{109}$, Ser$^{218}$]. Double-stranded DNA from this bacteriophage was digested with HindIII and KpnI in combination, then a 750 bp fragment carrying the four mutations of the aprA-subtilisin gene was ligated to pAMB106 which had been previously digested with HindIII and KpnI. The resulting plasmid, pAMB133, may be introduced into B. subtilis host cells for synthesis and secretion of [Asp$^{76}$, Glu$^{79}$, Ser$^{109}$, Ser$^{218}$]-subtilisin.

EXAMPLE 9

Figure 5:
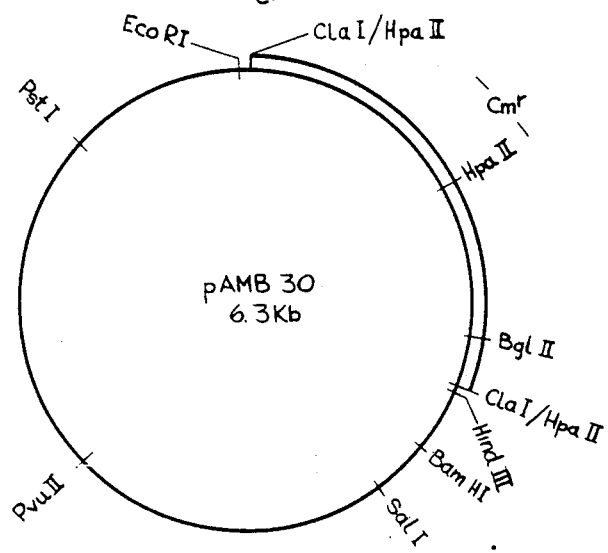
FIG. 5 is a partial restriction map of pAMB30 plasmid.

Because most Bacilli secrete alkaline and/or neutral proteases into the surrounding growth medium, it is preferable that mutations be introduced into endogenous alkaline and neutral protease genes of B. subtilis to block their synthesis so that mutated subtilisin genes, when introduced into the mutant cell, may produce mutated subtilisins which will then be secreted in a medium free of other proteases likely to interfere with isolation of intact subtilisin analogs. Two mutant B. subtilis strains BZ24 and BZ25, which produce no detectable extra cellular proteases, were constructed in accordance with the following procedure:

First, a plasmid vehicle capable of replicating in E. coli, but not in B. subtilis unless integrated into the B. subtilis chromosome by homologous recombination, was constructed as follows. Plasmid pBD64 (Bacillus Genetic Stock Center, Number 1E22) was digested to completion with HpaII to produce three fragments of 2.95 kb, 1.0 kb and 0.75 kb in size. These fragments were then ligated as a mixture to plasmid pBR322 (A.T.C.C. 37017) which previously had been digested with ClaI. The ligation products were introduced into E. coli C600 (available from the American Type Culture Collection as A.T.C.C. 23724) by transformation [Mandel, et al., J. Mol. Biol., 53, 154 (1970)]. Selection was for cells resistant to chloramphenicol (20 μg/ml) and ampicillin (50 μg/ml). Plasmid DNA from 12 transformants was prepared by an alkaline extraction procedure described by Birnboim, et al., Nucleic Acids Res., 7, 1513–1523 (1979), then digested with HindIII and EcoRI in combination to verify the presence of inserted fragment(s). One such plasmid, designated pAMB30, was found to carry the 1.0 and 0.75 kb HpaII fragments of pBD64 in the ClaI site of pBR322. These fragments contain the chloramphenicol acetyltransferase (cat) gene which is functional in E. coli and B. subtilis. Digestions with BglII and, separately, with Sau3A confirmed the identity and orientation of the cat gene on pAMB30, as illustrated in FIG. 5.

Because pAMB+ lacks an origin of replication sequence which is functional in B. subtilis, it cannot replicate as an autonomous replicon in B. subtilis host cells. On the other hand, pAMB30 contains the pBR322-derived origin of replication which is functional in E. coli, thus the plasmid can be propagated in E. coli host cells. Plasmid pAMB30 is useful in at least 2 ways. First, a fragment of DNA which contains a functional origin of replication in B. subtilis may be detected when cloned onto pAMB30 such that the plasmid will autonomously replicate in the extrachromosomal state. Second, plasmid pAMB30 can integrate into the genome of B. subtilis at a site of homology between the chromosome and B. subtilis DNA cloned onto pAMB30. This has been demonstrated by Haldenwang, et al., J. Bacteriol., 142, 90–98 (1980) and Young, J. Gen. Microbiol., 129, 1497–1512 (1983) using plasmid vehicles similar to, but not identical to pAMB30.

Plasmid pAMB21 (described in Example 1) was digested with EcoRI and PstI to isolate the xylE gene on a 1.0 kb fragment. The fragment was ligated to pAMB30 which had been previously digested with EcoRI and PstI. Ligation products were introduced into E. coli C600 by transformation. Selection was for chloramphenicol resistant (20 μg/ml) host cells which were sensitive to ampicillin (50 μg/ml) due to the insertion of the xylE fragment of pAMB21 into the structural gene for ampicillin resistance of pAMB30. The resulting plasmid, pAMB30/21, has properties identical to pAMB30 but has, in addition, a functional xylE gene.

Plasmid pAMB110, which carries the aprA gene deleted of a region coding for the latter 226 amino acids of mature subtilisin, was digested with EcoRI and KpnI. The 1.9 kb fragment of B. subtilis DNA containing genetic regulatory sequences for aprA gene expression, "the pre-pro" region, the DNA sequence coding for the first 49 amino acids of mature subtilisin and 3' non-coding sequences was ligated to pAMB30/21 that had been previously digested with EcoRI and KpnI. Ligation products were introduced into *E. coli* C600 by transformation. Plasmid DNA from several transformants was isolated by the alkaline extraction procedure of Birnboim, et al., supra, and the presence of the inserted 1.9 kb fragment was verified by multiple restriction endonuclease digestions. One such plasmid, designated pAMB301, was retained for further use.

*B. subtilis* strain BGSC1A274 (Bacillus Genetic Stock Center) carries a mutation at the npr locus and is incapable of producing extra cellular neutral protease. The plasmid pAMB301 was integrated into the genome of *B. subtilis* BGSC1A274 by transformation of competent cells [Spizizen, *Proc. Natl. Acad. Sci. (USA)*, 44, 1072–1078 (1958)]. Selection was for chloramphenicol-resistant (5 μg/ml) host cells which were then transferred by sterile toothpicks to L-agar supplemented with 1.5% (w/v) powdered skim milk and (5 μg/ml) cloramphenicol. Those cells which failed to produce a clear halo surrounding the colony were deficient in the ability to produce extracellular neutral and serine proteases due to the combination of the npr mutation along with the newly introduced aprA mutation. The aprA mutation was a deletion of the latter 226 amino acids of mature subtilisin due to the replacement of the wild-type aprA gene with the deleted version carried on pAMB301. One such strain, designated BZ24, has the Npr⁻ Apr⁻ Cm$^r$ phenotype, thus it produces no detectable extracellular neutral protease nor extracellular alkaline protease and is resistant to chloramphenicol at 5 μg/ml. Southern blotting [Southern, *J. Mol. Biol.*, 98, 503–517 (1975)] was used to confirm the deletion in the aprA gene on the chromosome of *B. subtilis* BZ24. Cultivation of *B. subtilis* BZ24 in Antibiotic Medium No. 3 (Penassay Broth, Difco, Detroit, Michigan) in the absence of antibiotic selection for approximately 32 generations led to the isolation of a derivative strain of BZ24 in which the cat gene confering chloramphenicol resistance upon host cells was lost due to its instability in the BZ24 chromosome. Such a phenomenon has been previously observed by Stahl, et al., *J. Bacteriol.*, 158, 411–418 (1984). A chloramphenicol-sensitive derivative of BZ24 was designated BZ25. *B. subtilis* BZ25 has the Npr⁻ Apr⁻ phenotype, thus it produces no detectable extracellular neutral protease nor extracellular alkaline protease. Southern blotting was used to confirm the deletion in the aprA gene on the chromosome of *B. subtilis* BZ25.

Because *B. subtilis* BZ25 produces no detectable extracellular neutral protease nor subtilisin, it is a useful host strain for introduction of plasmid DNA, such as pAMB113, for the production of mutated subtilisins which may be secreted into the surrounding growth medium free of other proteases.

*B. subtilis* BZ25 produces no detectable extracellular protease when culture supernatants are assayed as described below. *B. subtilis* BZ25/pAMB113, which is BZ25 that harbors plasmid pAMB113 (introduced by the protoplast transformation method of Chang, et al., supra) produces appreciable quantities of [Ser$^{218}$]-subtilisin when culture supernatants are assayed as described.

EXAMPLE 10

Integration of the [Ser$^{218}$]-subtilisin gene into the chromosome of *B. subtilis* was believed to provide an efficient way of increasing the genetic stability of this mutant gene. Such as approach also alleviates the requirement for chloramphenicol in the fermentation medium which is otherwise needed for application of selective pressure to maintain plasmid DNA in the extrachromosomal state. Therefore, the [Ser$^{218}$]-subtilisin gene, along with its genetic regulatory sequences and flanking DNA homologous to the *B. subtilis* chromosome, was isolated from a low melting point agarose gel after electrophoresis of pAMB113 which had been digested with EcoRI and PstI in combination. The 4.0 kb EcoRI to PstI fragment (illustrated in FIG. 4) was then ligated to pAMB30 (illustrated in FIG. 5) which had been digested with EcoRI and PstI in combination. Ligation products were introduced into *E. coli* HB101 (A.T.C.C. 33694) by transformation. Selection was for cells resistant to chloramphenicol (20 μg/ml). Plasmid DNA from four transformants which met the criteria above were isolated by the alkaline extraction procedure of Birnboim, et al., supra, then digested with EcoRI and PstI in combination. All four plasmids contained the 4.0 kb insert and the 5.6 kb remaining portion of pAMB30. One such plasmid, designated pAMB302, was purified and retained for further use.

Repeated attempts to integrate plasmid pAMB302 into the chromosome of *B. subtilis* BZ25 by the competence method [Spizizen, supra] were unsuccessful. This may have been due to the failure of BZ25 cells to become competent by the method employed. Therefore, pAMB302 was introduced into *B. subtilis* BZ25 cells by the protoplast transformation method of Chang, et al., supra. This result is particularly significant in that research strains in which integration has been obtained were selected on the basis of transformation by the competence method. Strains which may be unable to become competent, and in particular industrial strains which were not selected on the basis of transformation by the competence method, may be more likely to be unable to become competent.

Selection was for chloramphenicol-resistant cells (5 μg/ml) cells, which were then transferred with sterile toothpicks to L-agr supplemented with 1.5% (w/v) skim milk and 5 μg/ml chloramphenicol. Cells were incubated overnight at 37° C. Clear halos of different diameters were observed around the Cm$^r$ colonies. This indicates that subtilisin was produced and secreted by these cells. An attempt was made to isolate plasmid DNA from eight of these colonies by the alkaline extraction method. No plasmid DNA was detected on agarose gels which were stained with ethidium bromide (1 μg/ml) to visualize DNA after electrophoresis. The absence of extrachromosomal plasmid DNA in the Cm$^r$ cells which produced subtilisin was a strong indication that pAMB302 had been integrated into the chromosome of *B. subtilis*.

Several colonies resulting from this experiment were isolated and designated BZ28, BZ29, BZ30, BZ31, BZ32 and BZ33. Each strain was grown overnight at 37° C. with vigorous shaking in brain heart infusion medium (BHI, Difco) supplemented with 5 μg/ml chloramphenicol. Culture supernatants were assayed for subtilisin activity. *B. subtilis* strains BZ28, BZ29, BZ30, BZ31, BZ32 and BZ33 all produced subtilisin and secreted it into the surrounding growth medium, some strains producing more than others. The amount of subtilisin observed in the liquid culture broth was directly proportional to the size of the halo observed on skim milk L-agar plates. Because of the amounts of subtilisin secreted by these cells differed, multiple copies of pAMB302 were integrated into the chromosome or gene amplification [Young, *J. Gen. Microbiol.*, 129, 1497-1512 (1983); Albertini, et al., *J. Bacteriol.*, 162, 1203-1211 (1985)] had taken place.

EXAMPLE 11

Wild-type subtilisin, from BZ25/pAMB111, and [$Asp^{76}$, $Ser^{109}$, $Ser^{218}$]-subtilisin analog, from BZ25/pAMB131, were isolated and purified as follows. Each culture broth was centrifuged at 15,000 g for 30 minutes and protein in the clear supernatant was precipitated with $(NH_4)_2SO_4$ (350 g per liter). The precipitate was collected by centrifugation, triturated with 75% acetone, filtered and dried under vacuum.

In order to further purify the enzyme, the dried precipitate was dissolved in water and the solution was filtered and then dialyzed against 0.02M sodium phosphate buffer at pH 6.3. The dialyzed solution was passed through a column (2.5×15 cm) of carboxymethyl cellulose at a rate of 2 ml per minute. After washing the column with 0.02M sodium phosphate (pH 6.3), the enzyme was eluted with the same buffer containing 0.15M NaCl. Peak fractions were pooled and protein from the fractions containing the enzyme, as identified by a color change in a sample of the fraction mixed with succinyl-L-alanyl-L-alanyl-L-prolyl-L-phenylalanyl-p-nitroanilide (Vega Biochemicals), were precipitated by addition of 2.5 volumes of acetone. The precipitate was collected by centrifugation and then dissolved in 0.005M calcium acetate (about 1 ml per 10 mg). The resulting solution was dialyzed at 4° C. against water and then lyphilized.

EXAMPLE 12

Pure subtilisin or subtilisin analog was applied to a FPLC Superose 12 column, and the material eluting as the intact (not cleaved) protein was pooled, in 20 mM MES, 0.1M NaCl, 10 mM $CaCl_2$, pH 6.3. Samples of wild type subtilisin, or subtilisin analog of the present invention to be evaluated were incubated for 10 min. in the same buffer, the buffer +3% SDS, or 20 mM MES, 0.1M NaCl, 5 mM $CaCl_2$ and 15 mM EDTA at the indicated temperature. The samples were cooled to room temperature for 5 min. and then assayed for 20 min. at room temperature (20° C.) in Tris-HCl, pH 8.0 with 0.6% azocasein to determine proteolytic activity. The proteolytic activity of each sample is expressed as a percentage of the original activity of either wild type or analog, at 20° C. in 10 mM $CaCl_2$, and is represented in Table 2.

TABLE 2

| Temperature | 0% SDS | 3% SDS | 0% SDS +15 mM EDTA |
|---|---|---|---|
| Proteolytic Activity of Wild Type Subtilisin | | | |
| 20 | 100 | 8 | 100 |
| 35 | 100 | 0 | 62 |
| 50 | 95 | 0 | 37 |
| 70 | 14 | 0 | 14 |
| 100 | 0 | 0 | 0 |
| Activity of [$Asp^{76}$, $Ser^{109}$, $Ser^{218}$] Subtilisin Analog of Example 5 | | | |
| 20 | 100 | 55 | 91 |
| 50 | 100 | 12 | 94 |
| 100 | 5 | 0 | 5 |

EXAMPLE 13

Intact subtilisins were obtained by FPLC on the Superose 12 column. The intact subtilisins were incubated for 30 minutes at room temperature (20° C.) in 15 mM MES, 0.05M NaCl, pH 6.3 containing either 4 mM $CaCl_2$ or 4 mM EDTA, and a varied amount of SDS. The proteolytic activity of the enzyme was then determined by a 20 min. incubation in 0.6% azocasein in Tris-Cl, pH 8.0. The proteolytic activity of each sample evaluated is expressed in Table 3 as a percentage of the original activity of the sample in 0% SDS and 10 mM $Ca^{2+}$.

TABLE 3

| % SDS | 4 mM $Ca^{2+}$ | 4 mM EDTA |
|---|---|---|
| Proteolytic Activity of Wild Type Subtilisin | | |
| 0 | 100 | 94 |
| 0.1 | 100 | 76 |
| 0.25 | 100 | 45 |
| 0.50 | 76 | 13 |
| 0.75 | 63 | 3 |
| 1.0 | 60 | 0 |
| 2.0 | 29 | 0 |
| 3.0 | 17 | 0 |
| Proteolytic Activity of [$Asp^{76}$, $Ser^{109}$, $Ser^{218}$] Subtilisin Analog | | |
| 0 | 100 | 95 |
| 0.1 | 100 | 95 |
| 0.25 | 100 | 86 |
| 0.50 | 100 | 81 |
| 0.75 | 96 | 79 |
| 1.0 | 96 | 78 |
| 2.0 | 86 | 69 |
| 3.0 | 71 | 65 |

EXAMPLE 14

The stabilities of [$Asp^{76}$, $Ser^{109}$, $Ser^{218}$] subtilisin analog, [$Asp^{76}$, $Glu^{79}$, $Ser^{109}$, $Ser^{218}$] subtilisin analog and subtilisin Carlsberg were evaluated at three temperatures (25° C., 37° C. and 50° C.) in two buffer solutions (0.06M sodium phosphate, pH 9.0 or 0.12M sodium glycinate, pH 11.0). The results are expressed in Table 4 as half-life of the enzymes under the specified conditions.

TABLE 4

| Subtilisin | $t_{\frac{1}{2}}$ (25° C.) | $t_{\frac{1}{2}}$ (37° C.) | $t_{\frac{1}{2}}$ (50° C.) |
|---|---|---|---|
| A. In 0.12 M sodium glycinate pH 11.0 + 0.2% SDS. | | | |
| [$Asp^{76}$, $Ser^{109}$, $Ser^{218}$] analog | 110 days | 35.2 hrs | 6.7 hrs |
| subtilisin Carlsberg | 2 days | 8.4 hrs | 0.53 hr |
| [$Asp^{76}$, $Glu^{79}$, $Ser^{109}$, $Ser^{218}$] analog | 154 days | 35.3 hrs | 7.8 hrs |
| B. In 0.06 M sodium phosphate pH 9.0 + 0.2% SDS. | | | |
| [$Asp^{76}$, $Ser^{109}$, $Ser^{218}$] analog | 79.2 hrs | 16.0 hrs | 0.52 hr |
| subtilisin Carlsberg | 17.3 hrs | 2.4 hrs | 0.18 hr |
| [$Asp^{76}$, $Glu^{79}$, $Ser^{109}$, $Ser^{218}$] analog | 86.3 hrs | 22.0 hrs | 0.96 hr |
| C. In 0.12 M sodium glycinate pH 11.0 + 5 mM EDTA. | | | |
| [$Asp^{76}$, $Ser^{109}$, $Ser^{218}$] analog | 28.7 hrs | 1.87 hrs | 0.25 hr |
| subtilisin Carlsberg | 24 hrs | 1.71 hrs | 0.45 hr |

TABLE 4-continued

| Subtilisin | t½ (25° C.) | t½ (37° C.) | t½ (50° C.) |
|---|---|---|---|
| [Asp$^{76}$, Glu$^{79}$, Ser$^{109}$, Ser$^{218}$] analog | 21.5 hrs | 1.42 hrs | 0.20 hr |
| D. In 0.06 M sodium phosphate pH 9.0 + 5 mM EDTA. | | | |
| [Asp$^{76}$, Ser$^{109}$, Ser$^{218}$] analog | 27.4 hrs | 1.75 hrs | 0.23 hr |
| subtilisin Carlsberg | 26.3 hrs | 1.68 hrs | 0.32 hr |
| [Asp$^{76}$, Glu$^{79}$, Ser$^{109}$, Ser$^{218}$] analog | 19.7 hrs | 1.36 hrs | 0.17 hr |

While the present invention has been described in terms of preferred embodiments it is understood that modifications and improvements will occur to those skilled in the art. Thus, it is expected that substitution of residues at calcium binding sites other than at the specific calcium described herein may improve stability as well. Additional improvements in stability are expected for such substitutions made in other enzymes which have the Asn-Gly sequence and in other proteins comprising this sequence. Furthermore, it is expected that a subtilisin analog according to the present invention possesses superior properties to wild type subtilisins in detergent formulations such as those disclosed in, for example, U.S. Pat. No. 3,732,170; U.S. Pat. No. 3,749,671 and U.S. Pat. No. 3,790,482, all of which are incorporated by reference herein.

Moreover, for practical reasons many industrial processes are conducted at temperatures that are above the stability temperature range of most enzymes. Therefore, although detergent applications have been emphasized herein, it is believed that thermostable subtilisin analogs according to the present invention are not only advantageous to certain industries such as detergent industry, which already require stable subtilisins, but also may be useful in industries that use chemical means to hydrolyze proteins, e.g., hydrolysis of vegetable and animal proteins for the production of soup concentrates.

Therefore, it is intended that the present invention include all such modifications and improvements as come within the scope of the present invention as claimed.

What is claims is:

1. A subtilisin analog having an amino acid sequence of a naturally occurring Bacillus subtilisin that has been modified by having:
   (1) one or more of the amino acids present in the calcium binding site of the naturally occurring Bacillus subtilisin represented by Asp$^{41}$, Leu$^{75}$, Asn$^{76}$, Asn$^{77}$, Ser$^{78}$, Ile$^{79}$, Gly$^{80}$, Val$^{81}$, Thr$^{208}$, and Tyr$^{214}$ replaced by a negatively charged amino acid; and
   (2) one or more of the amino acids comprising any Asn-Gly sequence of the naturally occurring Bacillus subtilisin deleted or replaced by a different amino acid.

2. A subtilisin analog according to claim 1 wherein the analog is an analog of a naturally occurring Bacillus subtilisin selected from the group consisting of subtilisin Carlsberg, subtilisin DY, subtilisin BPN', an aprA subtilisin of *Bacillus subtilis* and subtilisin from *Bacillus mesentericus*.

3. A subtilisin analog according to claim 1 wherein the negatively charged amino acid is Asp or Glu.

4. A subtilisin analog according to claim 3 having Asn$^{76}$ replaced with Asp$^{76}$.

5. A subtilisin analog according to claim 3 having Asn$^{77}$ replaced with Asp$^{77}$.

6. A subtilisin analog according to claim 3 having Ile$^{79}$ replaced with Glu$^{79}$.

7. A subtilisin analog according to claim 3 having Asn$^{76}$ replaced with Asp$^{76}$ and Asn$^{77}$ replaced with Asp$^{77}$.

8. A subtilisin analog according to claim 3 having Asn$^{76}$ replaced with ASP$^{76}$ and Ile$^{79}$ replaced with Glu$^{79}$.

9. A subtilisin analog according to claim 1 wherein an Asn residue in the Asn-Gly sequence is replaced by a residue of a different amino acid.

10. The analog as recited in claim 9 wherein an Asn residue in said Asn-Gly sequence is replaced by a residue of an amino acid from the group consisting of Ser, Val, Thr, Cys, Glu and Ile.

11. A subtilisin analog according to claim 10 wherein the Asn residue in the Asn-Gly sequence is replaced by Ser.

12. A subtilisin analog according to claim 11 wherein an Asn residue at position 109 is replaced by Ser.

13. A subtilisin analog according to claim 11 wherein an Asn residue at position 218 is replaced by Ser.

14. A subtilisin analog according to claim 11 wherein an Asn residue at positions 109 and 218 is replaced by Ser.

15. a subtilisin analog according to claim 14 selected from the group consisting of [Asp$^{76}$, Ser$^{109}$, Ser$^{218}$] subtilisin, [Asp$^{77}$, Ser$^{109}$, Ser$^{218}$] subtilisin, [Glu$^{79}$, Ser$^{109}$, Ser$^{218}$] subtilisin, [Asp$^{76}$, Asp$^{77}$, Ser$^{109}$, Ser$^{218}$] subtilisin and [Asp$^{76}$, Glu$^{79}$, Ser$^{109}$, Ser$^{218}$] subtilisin.

16. A subtilisin analog according to claim 1 wherein the Bacillus subtilisin has a naturally occurring amino acid sequence

```
                                                  -105
Met  Arg  Ser  Lys  Lys  Leu  Trp  Ile  Ser  Leu  Leu
GTG  AGA  AGC  AAA  AAA  TTG  TGG  ATC  AGC  TTG  TGG

Phe  Ala  Leu  Thr  Leu  Ile  Phe  Thr  Met  Ala  Phe
TTT  GCG  TTA  ACG  TTA  ATC  TTT  ACG  ATG  GCG  TTC

Ser  Asn  Met  Ser  Ala  Gln  Ala  Ala  Gly  Lys
AGC  AAC  ATG  TCT  GCG  CAG  GCT  GCC  GGA  AAA

Ser  Ser  Thr  Glu  Lys  Lys  Tyr  Ile  Val  Gly  Phe
AGC  AGT  ACA  GAA  AAG  AAA  TAC  ATT  GTC  GGA  TTT

Lys  Gln  Thr  Met  Ser  Ala  Met  Ser  Ser  Ala  Lys
AAA  CAG  ACA  ATG  AGT  GCC  ATG  AGT  TCC  GCC  AAG

Lys  Lys  Asp  Val  Ile  Ser  Glu  Lys  Gly  Gly  Lys
AAA  AAG  GAT  GTT  ATT  TCT  GAA  AAA  GGC  GGA  AAG

Val  Gln  Lys  Gln  Phe  Lys  Tyr  Val  Asn  Ala  Ala
GTT  CAA  AAG  CAA  TTT  AAG  TAT  GTT  AAC  GCG  GCC

Ala  Ala  Thr  Leu  Asp  Glu  Lys  Ala  Val  Lys
 GCA  GCA  ACA  TTG  GAT  GAA  AAA  GCT  GTA  AAA

Glu  Leu  Lys  Lys  Asp  Pro  Ser  Val  Ala  Tyr  Val
GAA  TTG  AAA  AAA  GAT  CCG  AGC  GTT  GCA  TAT  GTG

-1    +1
Glu  Glu  Asp  His  Ile  Ala  His  Glu  Tyr  Ala  Gln
GAA  GAA  GAT  CAT  ATT  GCA  CAT  GAA  TAT  GCG  CAA
```

-continued

```
                         10
Ser Val Pro Tyr Gly Ile Ser Gln Ile Lys Ala
TCT GTT CCT TAT GGC ATT TCT CAA ATT AAA GCG

20
Pro Ala Leu His Ser Gln Gly Tyr Thr Gly Ser
CCG GCT CTT CAC TCT CAA GGC TAC ACA GGC TCT

30
Asn Val Lys Val Ala Val Ile Asp Ser Gly Ile
AAC GTA AAA GTA GCT GTT ATC GAC AGC GGA ATT

40
Asp Ser Ser His Pro Asp Leu Asn Val Arg Gly
GAC TCT TCT CAT CCT GAC TTA AAC GTC AGA GGC

50
Gly Ala Ser Phe Val Pro Ser Glu Thr Asn Pro
GGA GCA AGC TTC GTA CCT TCT GAA ACA AAC CCA

60
Tyr Gln Asp Gly Ser Ser His Gly Thr His Val
TAC CAG GAC GGC AGT TCT CAC GGT ACG CAT GTA

70
Ala Gly Thr Ile Ala Ala Leu Asn Asn Ser Ile
GCC GGT ACG ATT GCC GCT CTT AAT AAC TCA ATC 80                                    90
Gly Val Leu Gly Val Ala Pro Ser Ala Ser Leu
GGT GTT CTG GGC GTA GCG CCA AGC GCA TCA TTA

100
Tyr Ala Val Lys Val Leu Asp Ser Thr Gly Ser
TAT GCA GTA AAA GTG CTT GAT TCA ACA GGA AGC

110
Gly Gln Tyr Ser Trp Ile Ile Asn Gly Ile Glu
GGC CAA TAT AGC TGG ATT ATT AAC GGC ATT GAG

120
Trp Ala Ile Ser Asn Asn Met Asp Val Ile Asn
TGG GCC ATT TCC AAC AAT ATG GAT GTT ATC AAC

130
Met Ser Leu Gly Gly Pro Thr Gly Ser Thr Ala
ATG AGC CTT GGC GGA CCT ACT GGT TCT ACA GCG

140
Leu Lys Thr Val Val Asp Lys Ala Val Ser Ser
CTG AAA ACA GTC GTT GAC AAA GCC GTT TCC AGC

150
Gly Ile Val Val Ala Ala Ala Ala Gly Asn Glu
GGT ATC GTC GTT GCT GCC GCA GCC GGA AAC GAA

160
Gly Ser Ser Gly Ser Thr Ser Thr Val Gly Tyr
GGT TCA TCC GGA AGC ACA AGC ACA GTC GGC TAC

170
Pro Ala Lys Tyr Pro Ser Thr Ile Ala Val Gly
CCT GCA AAA TAT CCT TCT ACT ATT GCA GTA GGT

180
Ala Val Asn Ser Ser Asn Gln Arg Ala Ser Phe
GCG GTA AAC AGC AGC AAC CAA AGA GCT TCA TTC 190                                    200
Ser Ser Ala Gly Ser Glu Leu Asp Val Met Ala
TCC AGC GCA GGT TCT GAG CTT GAT GTG ATG GCT

210
Pro Gly Val Ser Ile Gln Ser Thr Leu Pro Gly
CCT GGC GTG TCC ATC CAA AGC ACA CTT CCT GGA

220
Gly Thr Tyr Gly Ala Tyr Asn Gly Thr Ser Met
GGC ACT TAC GGC GCT TAT AAC GGA ACG TCC ATG

230
Ala Thr Pro His Val Ala Gly Ala Ala Ala Leu
GCG ACT CCT CAC GTT GCC GGA GCA GCA GCG TTA

240
Ile Leu Ser Lys His Pro Thr Trp Thr Asn Ala
ATT CTT TCT AAG CAC CCG ACT TGG ACA AAC GCG

250
Gln Val Arg Asp Arg Leu Glu Ser Thr Ala Thr
CAA GTC CGT GAT CGT TTA GAA AGC ACT GCA ACA

260
Tyr Leu Gly Asn Ser Phe Tyr Tyr Gly Lys Gly
TAT CTT GGA AAC TCT TTC TAC TAT GGA AAA GGG 270                  275
Leu Ile Asn Val Gln Ala Ala Ala Gln OC
TTA ATC AAC GTA CAA GCA GCT GCA CAA TAA TAG

TAAAAAGAAGCAGGTTCCTCCATACCTGCTTCTTTTTA

TTTGTCAGCATCCTGATGTTCCGGCGCATTCTC
```

17. A subtilisin analog according to claim 16, [Asp[76], Ser[109], Ser[218]] subtilisin.

18. A subtilisin analog according to claim 16, [Asp[77], Ser[109], Ser[218]] subtilisin.

19. A subtilisin analog according to claim 16, [Glu[79], Ser[109], Ser[218]] subtilisin.

20. A subtilisin analog according to claim 16, [Asp[76], Asp[77], Ser[109], Ser[218]] subtilisin.

21. a subtilisin analog according to claim 16, [Asp[76], Glu[79], Ser[109], Ser[218]] subtilisin.

22. a subtilisin analog having an amino acid sequence of a naturally occurring Bacillus subtilisin that has been modified by having one or more of the amino acids present in the calcium binding site of the naturally occurring Bacillus subtilisin represented by Asp[41], Leu[75], Asn[76], Asn[77], Ser[78], Ile[79], Gly[80], Val[81], Thr[208], and Tyr[214] replaced by a negatively charged amino acid.

* * * * *